US00PP30965P2

(12) United States Plant Patent
Barnes

(10) Patent No.: US PP30,965 P2
(45) Date of Patent: Oct. 22, 2019

(54) ***PETUNIA* PLANT NAMED 'BBTUN98901'**

(50) Latin Name: ***Petunia* X *hybrida***
Varietal Denomination: BBTUN98901

(71) Applicant: Brent D. Barnes, Riverside, CA (US)

(72) Inventor: Brent D. Barnes, Riverside, CA (US)

(73) Assignee: PLANT Z1 LLC, Bonsall, CA (US)

( * ) Notice: Subject to any disclaimer, the term of this patent is extended or adjusted under 35 U.S.C. 154(b) by 0 days.

(21) Appl. No.: 15/998,148

(22) Filed: Jul. 10, 2018

(51) Int. Cl.
*A01H 5/02* (2018.01)

(52) U.S. Cl.
USPC ..... Plt./356.21

(58) Field of Classification Search
USPC ..... Plt./356.21
CPC ... A01H 5/02; A01H 5/00; A01H 6/82; A01H 6/824; A01H 6/1424; A01H 6/42
See application file for complete search history.

*Primary Examiner* — June Hwu
(74) *Attorney, Agent, or Firm* — C. A. Whealy

(57) ABSTRACT

A new and distinct *Petunia* plant named 'BBTUN98901', characterized by its upright to outwardly spreading and mounding to eventually trailing plant habit; vigorous growth habit; freely branching habit; early and freely flowering habit; dark red purple-colored flowers; and good garden performance.

1 Drawing Sheet

Botanical designation: *Petunia* X *hybrida*.
Cultivar denomination: 'BBTUN98901'.

BACKGROUND OF THE INVENTION

The present invention relates to a new and distinct cultivar of *Petunia* plant, botanically known as *Petunia* X *hybrida* and hereinafter referred to by the name 'BBTUN98901'.

The new *Petunia* plant is a product of a planned breeding program conducted by the Inventor in Bonsall, Calif. The objective of the breeding program is to create new vigorous, freely-branching and uniformly mounding *Petunia* plants with early and freely flowering habit, unique attractive flowers and good garden performance.

The new *Petunia* plant originated from a cross-pollination made by the Inventor on Oct. 9, 2015 in Bonsall, Calif. of a proprietary seedling selection of *Petunia* X *hybrida* identified as code number 15PB573-01, not patented, as the female, or seed, parent with *Petunia* X *hybrida* 'KLEPH14248', disclosed in U.S. Plant Pat. No. 27,046, as the male, or pollen, parent. The new *Petunia* plant was discovered and selected by the Inventor as a single flowering plant within the progeny of the stated cross-pollination in a controlled greenhouse environment in Bonsall, Calif. on June 23, 2016.

Asexual reproduction of the new *Petunia* plant by vegetative terminal cuttings in a controlled greenhouse environment in Bonsall, Calif. since Jun. 25, 2016 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBTUN98901'. These characteristics in combination distinguish 'BBTUN98901' as a new and distinct *Petunia* plant:

1. Upright to outwardly spreading and mounding to eventually trailing plant habit.
2. Vigorous growth habit.
3. Freely branching habit.
4. Early and freely flowering habit.
5. Dark red purple-colored flowers.
6. Good garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more vigorous and larger than plants of the female parent selection.
2. Plants of the new *Petunia* are denser and bushier than plants of the female parent selection.
3. Plants of the new *Petunia* perform better in the garden than plants of the female parent selection.

Plants of the new *Petunia* can be compared to plants of the male parent, 'KLEPH14248'. In side-by-side comparisons, plants of the new *Petunia* differ primarily from plants of 'KLEPH14248' in the following characteristics:

1. Plants of the new *Petunia* are denser and bushier than plants of 'KLEPH14248'.
2. Plants of the new *Petunia* and 'KLEPH14248' differ in flower color as plants of 'KLEPH14248' have dark red-colored flowers.
3. Plants of the new *Petunia* perform better in the garden than plants of 'KLEPH14248'.

Plants of the new *Petunia* can be compared to plants of 'USTUNI6001', disclosed in U.S. Plant Pat. No. 17,730. In side-by-side comparisons, plants of the new *Petunia* differ primarily from plants of 'USTUNI6001' in the following characteristics:

1. Plants of the new *Petunia* are more vigorous and larger than plants of 'USTUNI6001'.
2. Plants of the new *Petunia* are denser and bushier than plants of 'USTUNI6001'.
3. Plants of the new *Petunia* and 'USTUNI6001' differ in flower color as plants of 'USTUNI6001' have bright pink-colored flowers.
4. Plants of the new *Petunia* perform better in the garden than plants of 'USTUNI6001'.

Plants of the new *Petunia* can be compared to plants of 'KL 1117', disclosed in U.S. Plant Pat. No. 25,485. In side-by-side comparisons, plants of the new *Petunia* differ primarily from plants of 'KL 1117' in the following characteristics:

1. Plants of the new *Petunia* are more vigorous and larger than plants of 'KL 1117'.
2. Plants of the new *Petunia* are denser and bushier than plants of 'KL 1117'.
3. Plants of the new *Petunia* and 'KL 1117' differ in flower color as plants of 'KL 1117' have white-colored flowers.
4. Plants of the new *Petunia* perform better in the garden than plants of 'KL 1117'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'BBTUN98901' grown in a container.

The photograph at the top of the sheet is a close-up view of a typical flowering plant of 'BBTUN98901'.

DETAILED BOTANICAL DESCRIPTION

The aforementioned photographs and following observations and measurements describe plants grown during the late winter and early spring in 11.5-cm containers in an acrylic-covered greenhouse in Carleton, Mich. and under cultural practices typical of commercial *Petunia* production. During the production of the plants, day and night temperatures ranged from 18° C. to 24° C. Plants were eleven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'BBTUN98901'.

Parentage:

*Female, or seed, parent.*—Proprietary seedling selection of *Petunia* X *hybrida* identified as code number 15PB573-01, not patented.

*Male, or pollen, parent.*—*Petunia* X *hybrida* 'KLEPH14248', disclosed in U.S. Plant Pat. No. 27,046.

Propagation:

*Type.*—Terminal vegetative cuttings.

*Time to initiate roots, summer.*—About three to four days at temperatures ranging from 17° C. to 29° C.

*Time to initiate roots, winter.*—About five to seven days at temperatures ranging from 17° C. to 21° C.

*Time to produce a rooted plant, summer.*—About three weeks at temperatures ranging from 17° C. to 29° C.

*Time to produce a rooted plant, winter.*—About four weeks at temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to eventually trailing plant habit; freely branching habit with about four primary lateral branches each with about two to three secondary lateral branches per primary lateral branch developing; dense and bushy appearance; pinching enhances development of lateral branches; vigorous growth habit.

*Plant height, soil level to top of foliar plane.*—About 14.5 cm.

*Plant height, soil level to top of floral plane.*—About 17 cm.

*Plant diameter* (*area of spread*).—About 26 cm by 29 cm.

*Lateral branches.*—Length: About 17 cm. Diameter: About 3 mm to 3.5 mm. Internode length: About 1 cm. Strength: Strong. Aspect: Initially upright then outwardly spreading, about 45° to 65° from vertical. Texture and luster: Pubescent; viscid; matte. Color, developing: Close to 144A. Color, developed: Close to 146A.

Leaf description:

*Arrangement.*—Alternate before flowering; opposite after flowers develop; leaves simple.

*Length.*—About 5.2 cm.

*Width.*—About 3.7 cm.

*Shape.*—Elliptical.

*Apex.*—Acute.

*Base.*—Attenuate.

*Margin.*—Entire.

*Texture and luster, upper and lower surfaces.*—Minute pubescence; matte.

*Venation pattern.*—Pinnate, arcuate.

*Color.*—Developing leaves, upper and lower surfaces: Close to 146B. Fully expanded leaves, upper surface: Close to 137A; venation, close to 146B. Fully expanded leaves, lower surface: Close to 146B; venation, close to 146B.

*Petioles.*—Length: About 7 mm. Diameter: About 3 mm. Strength: Moderately strong. Texture and luster, upper and lower surfaces: Minute pubescence; matte. Color, upper and lower surfaces: Close to 146B.

Flower description:

*Flower type and flowering habit.*—Single axillary salverform flowers; flowers face mostly upward to outwardly; freely flowering habit with about more than 56 flowers developing per plant during the flowering season.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About five to seven days; flowers persistent.

*Fragrance.*—Faint; sweet.

*Flower buds.*—Length: About 3.5 cm. Diameter: About 6 mm. Shape: Oblong, elongate. Texture and luster: Pubescent; matte. Color: More grey than 86D.

*Flower diameter.*—About 5 cm.

*Flower depth (height).*—About 3.8 cm.

*Throat diameter, distal.*—About 1.2 cm.

*Tube length.*—About 2.7 cm.

*Tube diameter, proximally.*—About 3 mm.

*Petals* .—Quantity and arrangement: Five petals fused in a single salverform whorl. Petal lobe length (from throat): About 2.3 cm. Petal lobe width: About 2.5 cm. Petal lobe shape: Fan-shaped to roughly triangular. Petal lobe apex: Acute. Petal lobe margin: Entire; slightly to moderately undulate. Petal lobe texture and luster, upper surface: Smooth, glabrous; velvety; slightly glossy. Petal lobe texture and luster, lower surface: Scattered pubescence; somewhat glossy. Throat texture and luster: Smooth, glabrous; glossy. Tube texture and luster: Pubescent; somewhat glossy. Color: When opening, upper surface: Close to 61B. When opening, lower surface: Close to 186C to 186D. Fully opened, upper surface: Close to 61B; venation, close to 60A; color becoming closer to 61C with development. Fully opened, lower surface: Close to 186B to 186C; venation, close to 195A; color becoming closer to 186C with development. Flower throat (inside): Close to 187D; venation, close to 187B. Flower tube (outside): Close to 187C; venation, close to 197B.

*Sepals.*—Quantity and arrangement: Five sepals fused in a single star-shaped whorl. Calyx length: About 1.3 cm. Calyx diameter: About 2.4 cm. Length: About 1.6 cm. Width: About 3 mm. Shape: Ligulate. Apex: Acute. Margin: Entire. Texture and luster, upper and lower surfaces: Minute pubescence; matte. Color: When opening and fully opened, upper surface: Close to 146A. When opening and fully developed, lower surface: Close to 146B.

*Peduncles.*—Length: About 1.6 cm. Width: About 1 mm. Strength: Strong. Angle: About 45° from the stem axis. Texture and luster: Pubescent; matte. Color: Close to 146B.

*Reproductive organs.*—Stamens: Quantity per flower: Five. Filament length: About 9 mm. Filament color: Close to 157B. Anther length: About 1 mm. Anther shape: Oval. Anther color: Close to 164C. Pollen amount: None observed. Pistils: Quantity per flower: One. Pistil length: About 1.7 cm. Style length: About 1.4 cm. Style color: Close to 145D. Stigma diameter: About 2 mm. Stigma shape: Round. Stigma color: Close to 146B. Ovary color: Close to 146D.

*Seeds and fruits.*—Seed and fruit development has not been observed on plants of the new *Petunia* to date.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'BBTUN98901' as illustrated and described.

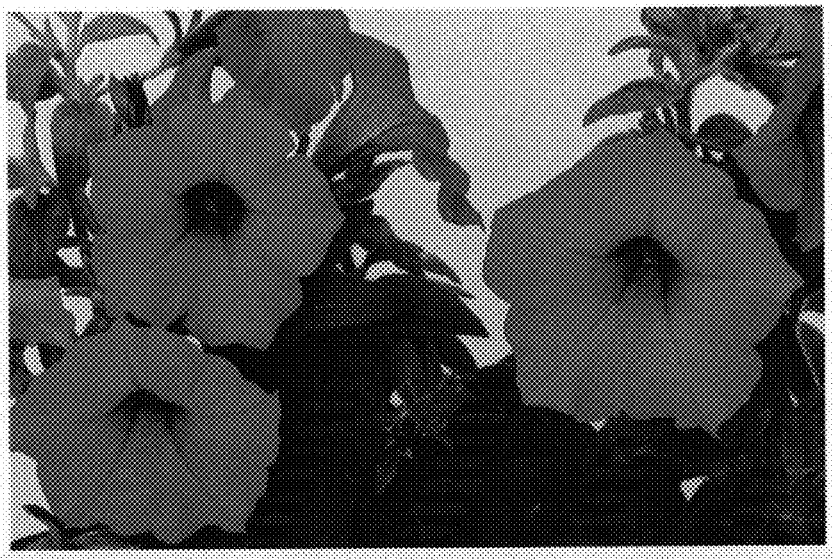
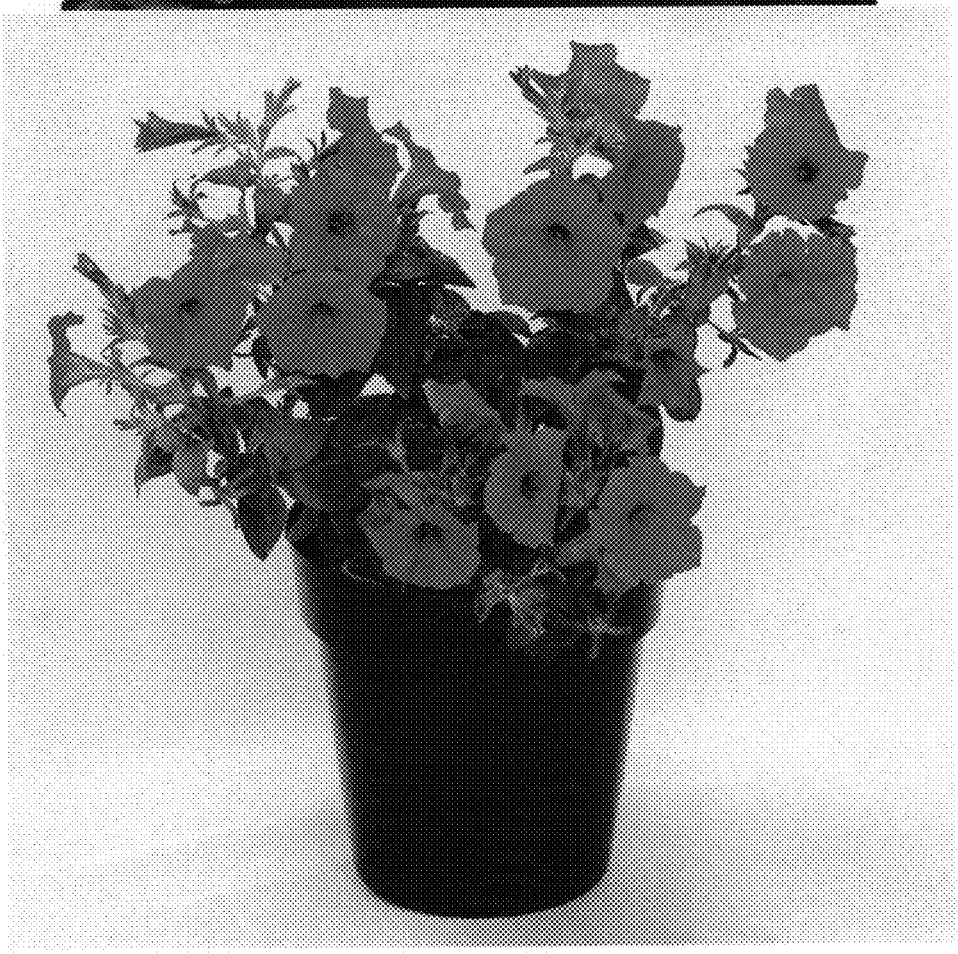

* * * * *